United States Patent
Paulus et al.

[11] Patent Number: 5,733,504
[45] Date of Patent: Mar. 31, 1998

[54] CATALYTIC/CERAMIC OXIDE MICROCOMPOSITES FOR USE AS EXHAUST SENSOR PRE-EQUILIBRATION ZONE

[75] Inventors: Nancy Jean Paulus; William John Paulus, both of Grand Blanc; Venkatesh Rajagopalan, Flint; Earl Wayne Lankheet, Grand Blanc, all of Mich.

[73] Assignee: General Motors Corporation, Detroit, Mich.

[21] Appl. No.: 557,669

[22] Filed: Nov. 13, 1995

Related U.S. Application Data

[63] Continuation-in-part of Ser. No. 198,322, Feb. 17, 1994, abandoned.

[51] Int. Cl.$^6$ ............... G01N 7/00; G01N 27/26; G05D 7/00; F01N 3/00
[52] U.S. Cl. ............... 422/83; 422/98; 422/107; 422/110; 204/291; 204/424; 204/428; 60/276; 60/285
[58] Field of Search .................. 422/82.08, 83, 422/88, 98, 177, 182, 183, 110, 107; 60/272, 276, 285; 204/424, 428, 291

[56] References Cited

U.S. PATENT DOCUMENTS

| | | | |
|---|---|---|---|
| 3,935,089 | 1/1976 | Togawa et al. | 204/195 S |
| 4,199,425 | 4/1980 | Sinkevitch | 204/195 S |
| 4,240,890 | 12/1980 | Watanabe et al. | 204/195 S |
| 4,249,156 | 2/1981 | Micheli | 338/34 |
| 4,279,782 | 7/1981 | Chapman et al. | 252/465 |
| 4,297,192 | 10/1981 | Shinohara et al. | 204/195 |
| 4,307,061 | 12/1981 | Serholz | 422/94 |
| 4,318,828 | 3/1982 | Chapman | 252/465 |
| 4,331,631 | 5/1982 | Chapman et al. | 422/180 |
| 4,382,323 | 5/1983 | Chapman et al. | 29/157 R |
| 4,394,301 | 7/1983 | Gardner | 252/455 Z |
| 4,507,397 | 3/1985 | Buss | 502/38 |
| 4,552,739 | 11/1985 | Kuhl | 423/328 |
| 4,704,494 | 11/1987 | Inji | 585/417 |
| 4,832,824 | 5/1989 | Vaughan et al. | 208/138 |

(List continued on next page.)

FOREIGN PATENT DOCUMENTS

| | | |
|---|---|---|
| A-0267765 | 5/1988 | European Pat. Off. . |
| A 0372425 | 6/1990 | European Pat. Off. . |
| A-0372425 | 6/1990 | European Pat. Off. . |
| 3813930A1 | 11/1988 | Germany . |
| 4004172A1 | 8/1990 | Germany . |
| WO93/06472 | 4/1993 | WIPO . |

OTHER PUBLICATIONS

Keiichi Saji et al., "Voltage step characteristics of oxygen concentration cell sensors for nonequilibrium gas mixtures"—Toyota Central Research and Development Laboratories, Inc., Nagakute–cho, Aichi–gun, Aichi, 480–11 Japan, vol. 135, No. 7; pp. 1686–1691.

A.D. Colvin et al, "Catalytic effects on $ZrO_2$ oxygen sensors exposed to non–equilibrium gas mixtures"—J. Electroanal. Chem., 136 (1982) 179–183.

J.E. Anderson et al., "Mass transfer effects on $ZrO_2$ oxygen concentration cells exposed to non–equilibrium $H_2$–$O_2$ mixtures"— Journal of Applied Electrochemistry 12 (1982) 463–467.

(List continued on next page.)

*Primary Examiner*—Nina Bhat
*Attorney, Agent, or Firm*—Cary W. Brooks

[57] ABSTRACT

The invention includes the use of a pre-equilibration zone on an exhaust gas sensor to provide catalytic site to catalyze non-reacted components of the exhaust gas prior to the gas sample reaching the sensor's outer electrode. The pre-equilibration zone has microcomposite which preferably includes a precious metal in a porous carrier such as a ceramic oxide. The invention also includes a method of making an exhaust sensor including a pre-equilibration zone, and a method of sampling an exhaust gas by passing the same through a pre-equilibration zone.

3 Claims, 7 Drawing Sheets

U.S. PATENT DOCUMENTS

| | | | |
|---|---|---|---|
| 4,863,583 | 9/1989 | Kurachi et al. | 204/424 |
| 4,888,105 | 12/1989 | Huss, Jr. et al. | 208/137 |
| 4,950,828 | 8/1990 | Shum | 585/417 |
| 5,077,970 | 1/1992 | Hamburg | 60/274 |
| 5,083,427 | 1/1992 | Anderson | 60/274 |
| 5,169,513 | 12/1992 | Mase et al. | 204/429 |

OTHER PUBLICATIONS

Patent Abstracts of Japan vol. 13 No. 314 (P–899) 18 Jul. 1989 & JP-A-01 083 149 (Japan Electronic Control Syst. Co) 28 Mar. 198 *abstract*.

Patent Abstract of Japan vol. 4 No. 43 (P–005) 4 Apr. 1980 & JP-A-55 013 828 (Toyota Motor Corp) 31 Jan. 1980 *abstract.

Patent Abstract of Japan vol. 6 No. 188 (P–144) (1066) 28 Sep. 1982 & JP-A-57 100 343 (Toyota Jidosha Kogyo K.K.) 22 Jun. 1982 *abstract*.

European Search Report corres to EP 95 20 0124 dated 18 May 1995 & Annex.

G. Baier et al, "Non–Nernstian Zirconia Sensors for Combuation Control", Appl.Phys. A57, 51–66 (1993).

J.E. Enderson et al, "Steady–State Characteristics of Oxygen Concentration Cell Sensors Subjected to Nonequilibrium Gas Mixtures", J Electrochem Soc vol. 128 No. 3 Feb. 1981 pp. 294–300.

L. Eltinge, "Fuel–Air Ratio and Distribution from Exhaust Gas Composition", SAE Paper 680114 pp. 425–450.

PRIOR ART

CATALYTIC/CERAMIC OXIDE MICROCOMPOSITES FOR USE AS EXHAUST SENSOR PRE-EQUILIBRATION ZONE

This is a continuation-in-part of application Ser. No. 08/198,322 filed on Feb. 17, 1994, now abandoned.

FIELD OF THE INVENTION

This invention relates to exhaust sensors, and more particularly to exhaust sensors including a catalytic/ceramic oxide microcomposite pre-equilibration zone.

BACKGROUND

Conventional coatings used in protective layer on the non-reference surface of a ceramic anion-conductor exhaust gas sensor are ordinarily composed of various non-catalyzed porous ceramic oxides, such as spinel. The primary functions of these coatings are to act both as a mechanical shield to prevent gas and particulate-induced erosion of a platinum electrode of the sensor and as a filter to reduce the rate at which poisoning from silica, lead and other harmful constituents in the exhaust stream can occur. It has been observed in the past, however, that porous non-catalytic coatings have contributed to non-ideal sensor performance. In particular, the coatings are known to accentuate "lean shift", a phenomenon in which unreacted gases resulting from incomplete combustion, present in the exhaust gas, causes the sensor to switch at an air/fuel ratio which is greater than the true stoichiometric point where lambda equals exactly unity. In addition to "lean shift", unreacted gases can also contribute to sensor output amplitude variation and they can amplify temperature sensitivity. Although some types of coatings and sensor packaging arrangements in the marketplace seem to minimize non-ideal sensor operating characteristics better than others, no satisfactory solution to the problem has been discovered heretofore.

The present invention overcomes the shortcomings of the prior art.

SUMMARY OF THE INVENTION

The invention includes the use of a pre-equilibration zone on an exhaust gas sensor to provide catalytic sites to catalyze the non-reacted components of the exhaust gas prior to the gas sample reaching the sensor's outer electrode. A microcomposite protective layer defines the equilibration zone and preferably includes a precious metal in a porous carrier such as a ceramic oxide. The invention also includes a method of making an exhaust sensor including a pre-equilibration zone, and a method of sampling an exhaust gas by passing the gas through a pre-equilibration zone.

These and other objects, features and advantages of the invention will become apparent from the following brief description of the drawings, detailed description and appended claims and drawings.

DETAILED DESCRIPTION

A pre-equilibration zone according to the present invention may be provided by a coating material of a microcomposite type including two distinct solid phases, a catalyst and a support which may be of porous material such as a ceramic oxide. The catalyst may take a variety of forms and preferably is an active metal such as palladium, platinum, rhodium, or transition metal such as nickel or mixtures of several such metals.

In a preferred method of preparing the pre-equilibration zone, an aqueous solution of any suitable soluble platinum salt such as $Pt(NH_3)_4CL_2$, tetraamineplatinum (II) chloride is prepared using deionized or distilled water. In a separate agitated vessel, a ceramic oxide component, such as that prepared from alumina, magnesia, spinel, zirconia powder or mixtures thereof is completely dispersed in a suitable quantity of deionized or distilled water. If necessary, a dispersing agent such as sodium polymethylmethacrylate may be added to the ceramic oxide/water system to insure dispersion. After the ceramic oxide component is completely dispersed in the deionized or distilled water, the platinum solution is titrated dropwise into the dispersion in the agitated vessel until the dry weight ratio of platinum-to-ceramic oxide ranges from about 1:5000 to about 1:4 and is preferably about 1:50, or 2.00 percent by weight platinum. The ratio of catalyst-to-ceramic oxide may also be expressed in terms of volume ratios for example using $ZrO_2$ and $Al_2O_3$ for the ceramic phase (Ox) in rhodium (Rh), and platinum (Pt) for the metallic phase (M) wherein the ratios expressed as M/(M+Ox). Using the following densities:

Density of Pt=21.45 $g/cm^3$

Density of RH=12.41 $g/cm^3$

Density of $ZrO_2$=5.89 $g/cm^3$

Density of $Al_2O_3$=3.96 $g/cm^3$

For 0.0002 weight percent M/Ox: This converts to a volume percent ranging between 0.00037 to 0.00064, depending upon constituents as listed below:

For $Rh/Rh+ZrO_2$ = (0.000002 g Rh/12.41 g/cc)/((0.000002 g Rh/ 12.41 g/cc) + (0.999998 g $ZrO_2$/5.89 g/cc))

= 0.000000161/(.000000161 · 10.1697789)

= 0.00000096 volume ratio

= 0.000096 volume percent

-continued

For Pt/ZrO$_2$ = (0.000002 g Pt/21.45 g/cc)/((0.000002 g Pt/21.45 g/cc) + (0.999998 g ZrO$_2$/5.89 g/cc))

= 0.000000093/(0.000000093 + 0.1697789)

= 0.00000055 volume ratio

= 0.000055 volume percent

For Rh/Al$_2$O$_3$ = (0.000002 g Rh/12.41 g/cc)/((0.000002 g Rh/12.41 g/cc) + (0.999993 g Al$_2$O$_3$/3.96 g/cc))

= 0.000000161/(.000000161 + 0.252524747)

= 0.0000064 volume ratio

= 0.00064 volume percent

For Pt/Al$_2$O$_3$ = 0.000002 g Pt to 1.000000 g Pt + Al$_2$O$_3$

= (0.000002 g Pt/21.45 g/cc)/((0.000002 g Rh/21.45 g/cc) + (0.999993 g Al$_2$O$_3$/3.96 g/cc))

= 0.000000093/(0.000000093 + 0.252524747)

= 0.00000037 volume ratio

= 0.000037 volume percent

For 20 weight percent M/Ox: This converts to a volume percent ranging between 4.4 to 10.6, depending upon constitutents as listed below:

For Rh/ZrO$_2$ = 0.2 g Rh to 1.00 g Rh + ZrO$_2$

= (0.2 g Rh/12.41 g/cc)/((0.2 g Rh/12.41 g/cc) + (0.8 g ZrO$_2$/5.89 g/cc))

= 0.016116/(0.016116 + 0.135823)

= 0.1060 volume ratio

= 10.6 volume percent

For Pt/ZrO$_2$ = (0.2 g Pt/21.45 g/cc)/((0.2 g Pt/21.45 g/cc) + (0.8 g ZrO$_2$/5.89 g/cc))

= .009324/(0.009324 + 0.135823)

= .0642 volume ratio

= 6.4 volume percent

For Rh/Al$_2$O$_3$ = (0.2 g Rh/12.41 g/cc)/((0.2 g Rh/12.41 g/cc) + (0.8 g Al$_2$O$_3$/3.96 g/cc))

= 0.016116/(.0161 + 0.20202)

= 0.073 volume ratio

= 7.3 volume percent

For Pt/Al$_2$O3 = 0.000002 g Pt to 1.000000 g Pt + Al$_2$O$_3$

= (0.2 g Pt/21.45 g/cc)/((0.2 g Rh/21.45 g/cc) + (0.8 g Al$_2$O$_3$/3.96 g/cc))

= 0.009324/(0.009324 + 0.20202)

= 0.0441 volume ratio

= 4.4 volume percent

Figure 4:
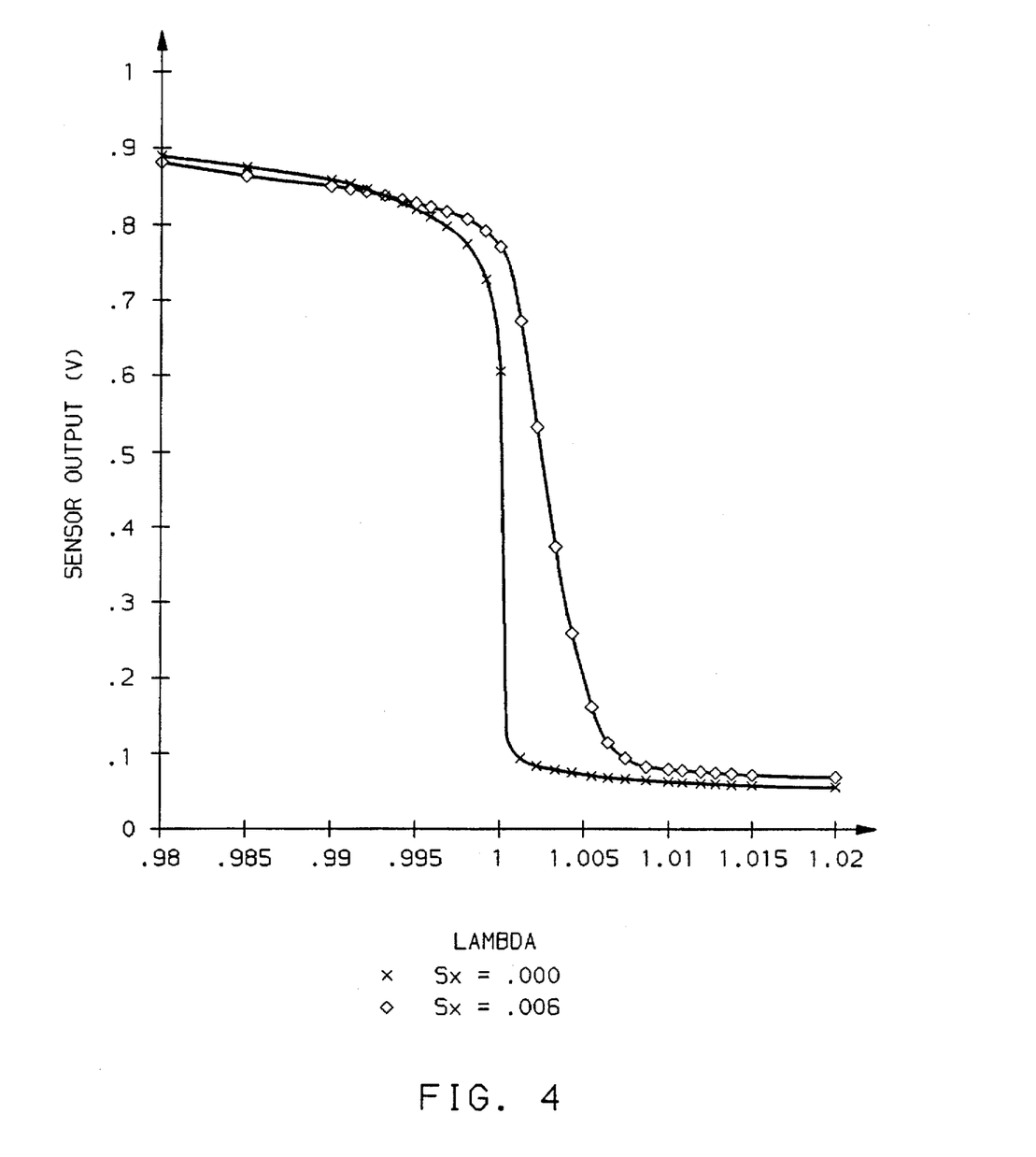
FIG. 4 is a graphic illustration of data obtained on the effect unreacted exhaust constituents on the output of a conical-shaped sensor with a microcomposite protective layer according to the present invention.
Figure 6:
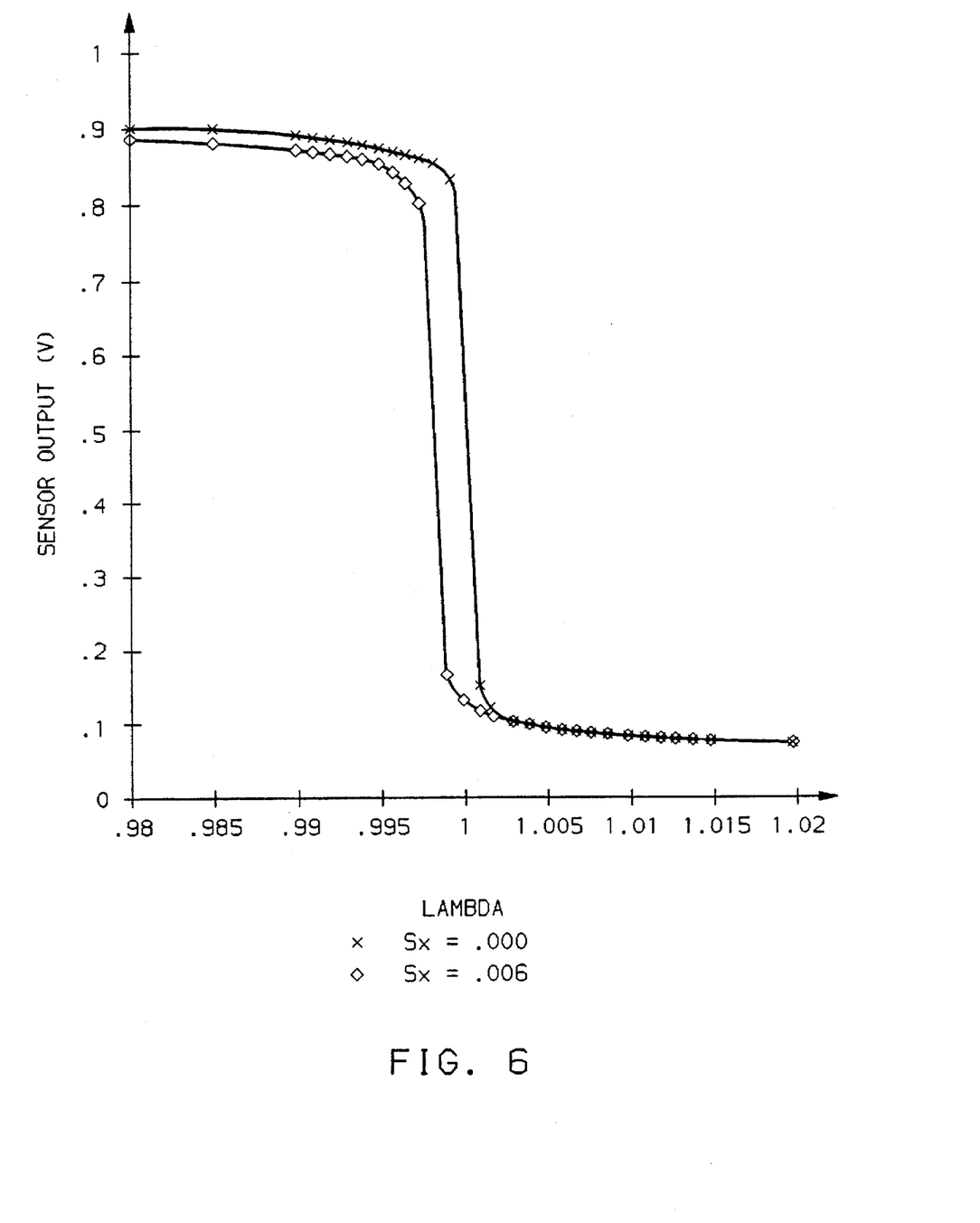
FIG. 6 is a graphic illustration of data obtained on the CO sensitivity of a conical-shaped sensor with a microcomposite protective layer according to the present invention.
Figure 8:
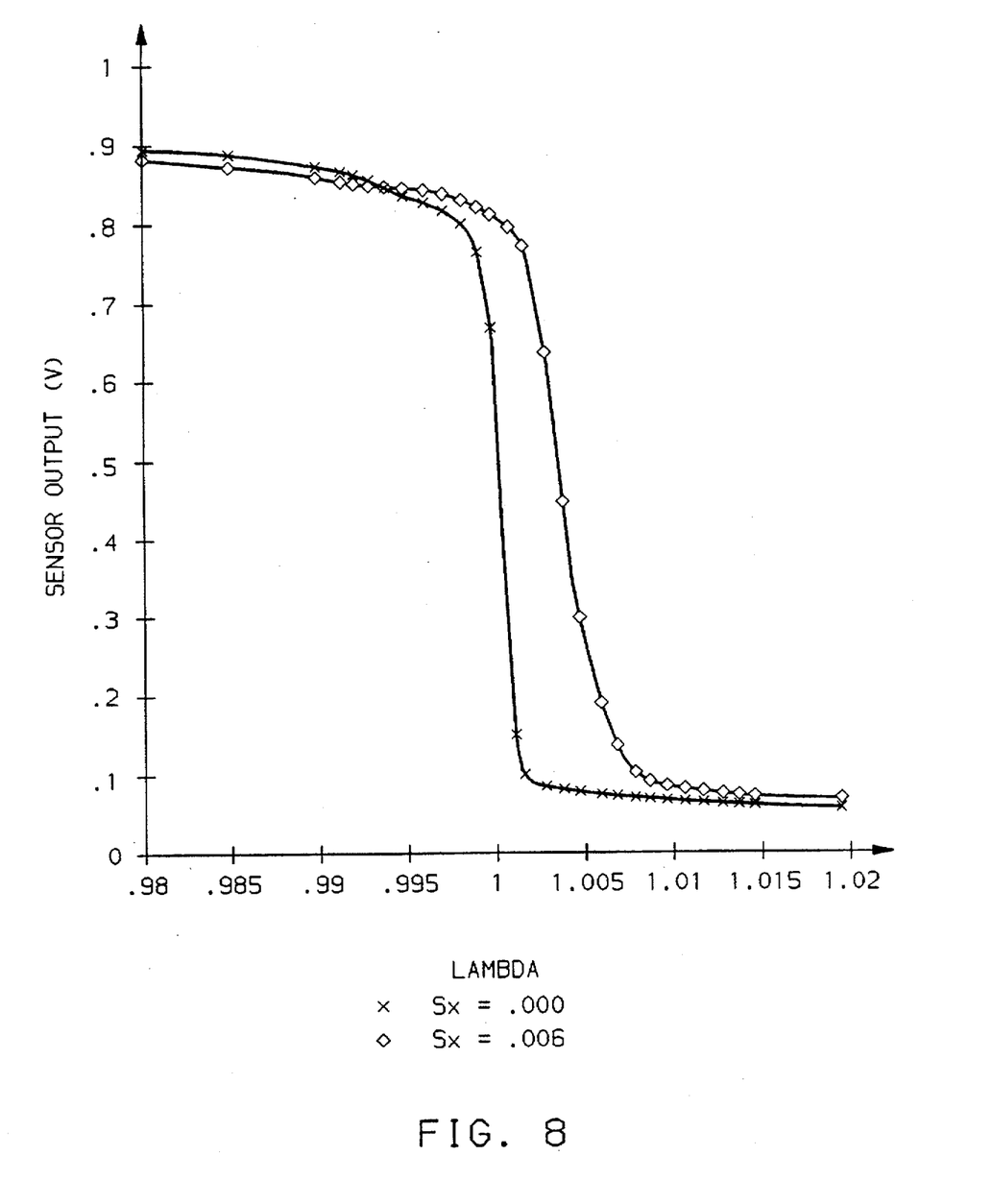
FIG. 8 is a graphic illustration of data on the hydrogen sensitivity of a conical-shaped sensor with a microcomposite protective layer according to the present invention.

As shown in FIGS. 4, 6, and 8, good results are obtained with about 1 weight percent platinum. The mixture is agitated for several minutes to insure that the tetraamineplatinum cations have ample opportunity to completely and evenly coat all of the exposed surfaces of the ceramic oxide powder. After mixing is complete, the mixture is dewatered back into a powder form using a convenient means of evaporation, such as by spray drying or by simple evaporation in an oven to form a platinum enriched powder. The platinum enriched powder can be screened to −200 mesh, transferred to a porcelain crucible or evaporation dish, and calcined in air in an ordinary vented furnace at about 500° C. for approximately 1 hour. The temperature of calcination is dependent upon the decomposition temperature of the precious metal containing salt chosen previously. At this stage, any residual volatiles are burned-off and the tetraamineplatinum ions dispersed over the surface of the ceramic particles undergo a redox reaction, giving up the amines as ammonia gas and leaving a very fine coating of platinum metal behind and bonded to the ceramic oxide.

After calcining as previously described, the catalytic coating precursor powder may be sieved again if necessary and stored in a covered container until ready to use. The precursor powder can be applied and permanently sintered over the outer electrode or protective coating of either a conical or flat plate exhaust gas sensor element in a variety of ways including (1) flame or plasma spraying; (2) dip-coated or cast; (3) screen printed; or (4) cast or roll compacted into a tape form and laminated over the top of the outer electrodes or protective coating.

The microcomposite resulting from the above processing of the precursor powder will have the catalytic properties discussed above throughout its bulk, i.e., from an external surface to its internal boundary with the sensor element's outer electrode or protective coating. This will insure that any unreacted constituents in the exhaust gas will have to pass through a relatively tortuous path within the catalytic porous structure before reaching the sensing electrode. This will provide an opportunity for the gas to pre-equilibrate, effectively reducing the chance that unreacted constituents will skew the output voltage of the sensor.

The thickness of the microcomposite layer forming the pre-equilibration zone may range from about 10 to about 500 microns depending upon the application, for example, preferably the pre-equilibration zone has a thickness ranging from 50–500 microns, 100–500 microns and most preferably 200–500 microns. The pre-equilibration zone must be thick enough to provide sufficient residence time for the exhaust gases to undergo catalysis by the metal in the pre-equilibration zone. Thereafter, the thickness of the pore ceramic protective coat 28 must be sufficiently thick to allow completion of the catalysis before the exhaust gas reaches the electrode 26. The thickness of the pore ceramic protective coat 28 is described hereafter. The porosity of the microcomposite layer may range from about 10% to about 60%. The particle size of the precursor powder may range from about $10^{-5}$ mm to about $10^0$ mm. The platinum in the dried precursor powder may range from about 0.002 to about 20 weight percent.

Alternatively, the pre-equilibration zone may be formed from catalytic microcomposites via post-impregnation. A post-impregnation process differs from a pre-impregnation process in that the ceramic oxide protective coat is already sintered and placed in a non-catalyzed form before the catalyst salt solution is introduced. It is therefore extremely easy to add these steps to a pre-existing exhaust sensor production process without requiring a major process changeover. As in the case before, this method will work with any catalytic material such as any precious or transition metal salt or mixtures of such salts in aqueous solution, but platinum again B will be used throughout this example. A tetraamineplatinum (II) chloride or other suitable solution containing 0.002 to 20 platinum by weight percent is applied by dipping, brushing or spraying or other convenient transfer method directly on the surface of the sintered protective coat. After allowing the solution to be pulled into the open pores of the coating from the exposed surface downward by capillary action the entire treated element may be dried and calcined to remove water and volatiles in the same way as described in the pre-impregnation section above. The remaining nanometer-scale platinum metal particles, having penetrated to the interior of the exposed pores, effectively forms a micro-network of catalyzed channels where before there was only exposed, relatively non-reactive ceramic surfaces. This again results in a novel microcomposite which will force any unreacted constituent such as $O_2$, CO, $H_2$, hydrocarbon and $NO_x$ in the exhaust gas to travel a relatively tortuous path through a heavily catalyzed porous structure. Again, the gas mixture will undergo pre-equilibration before reaching the sensing electrode to keep the skewed voltage output from the sensor at a minimum.

A protective cover coat electrically isolates the pre-equilibration zone microcomposite layer from the outer platinum electrode. The protective cover coat may have a thickness ranging from about 25 to about 500 micron and a porosity of about 10 to about 60%. For example, preferably the protective coat may have a thickness ranging from 50–500 microns, 100–500 microns and 200–500 microns. A suitable protective coat material includes spinel or alumina, or any porous ceramic. The outer electrode of the sensor is made from a porous material such as platinum and zirconia and is applied to an electrolyte body such as zirconia in a manner which is known to those skilled in the art. The inner electrode is also made from a porous material such as platinum and zirconia in a similar manner.

Figure 1:
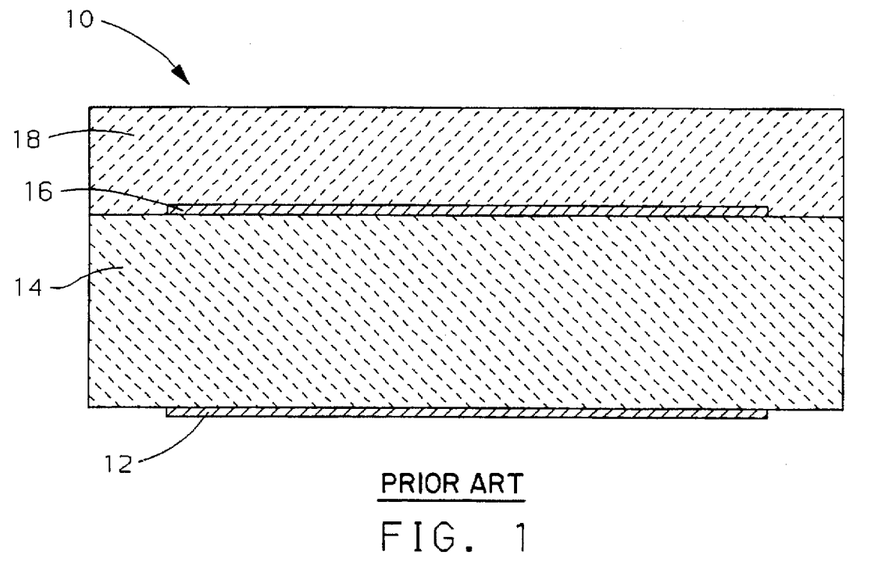
FIG. 1 is an illustration of a representative cross section of an ordinary exhaust sensing device.
Figure 3:
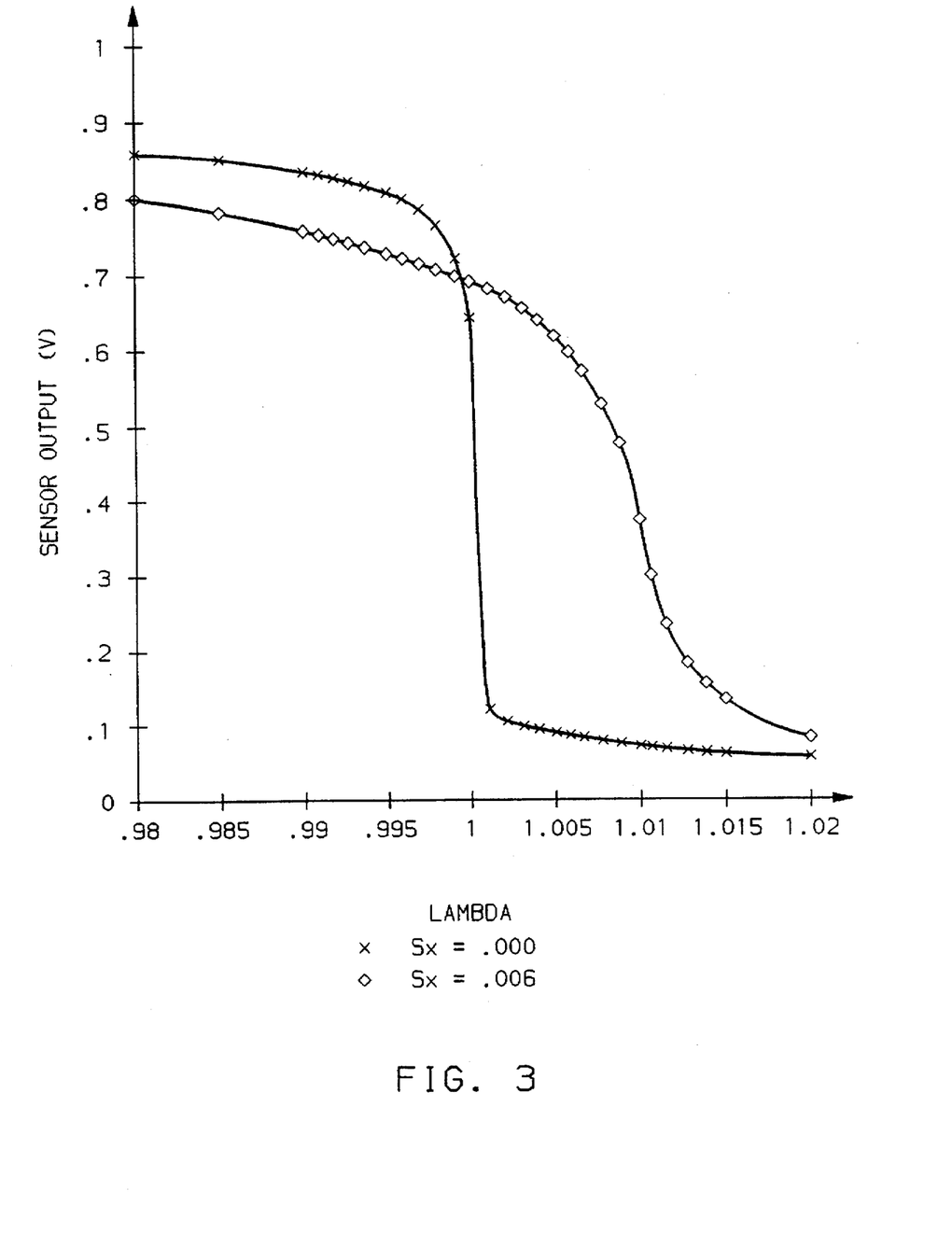
FIG. 3 is a graphic illustration of data obtained on the effect unreacted exhaust constituents on the output of a conical-shaped sensor without a microcomposite layer.
Figure 5:
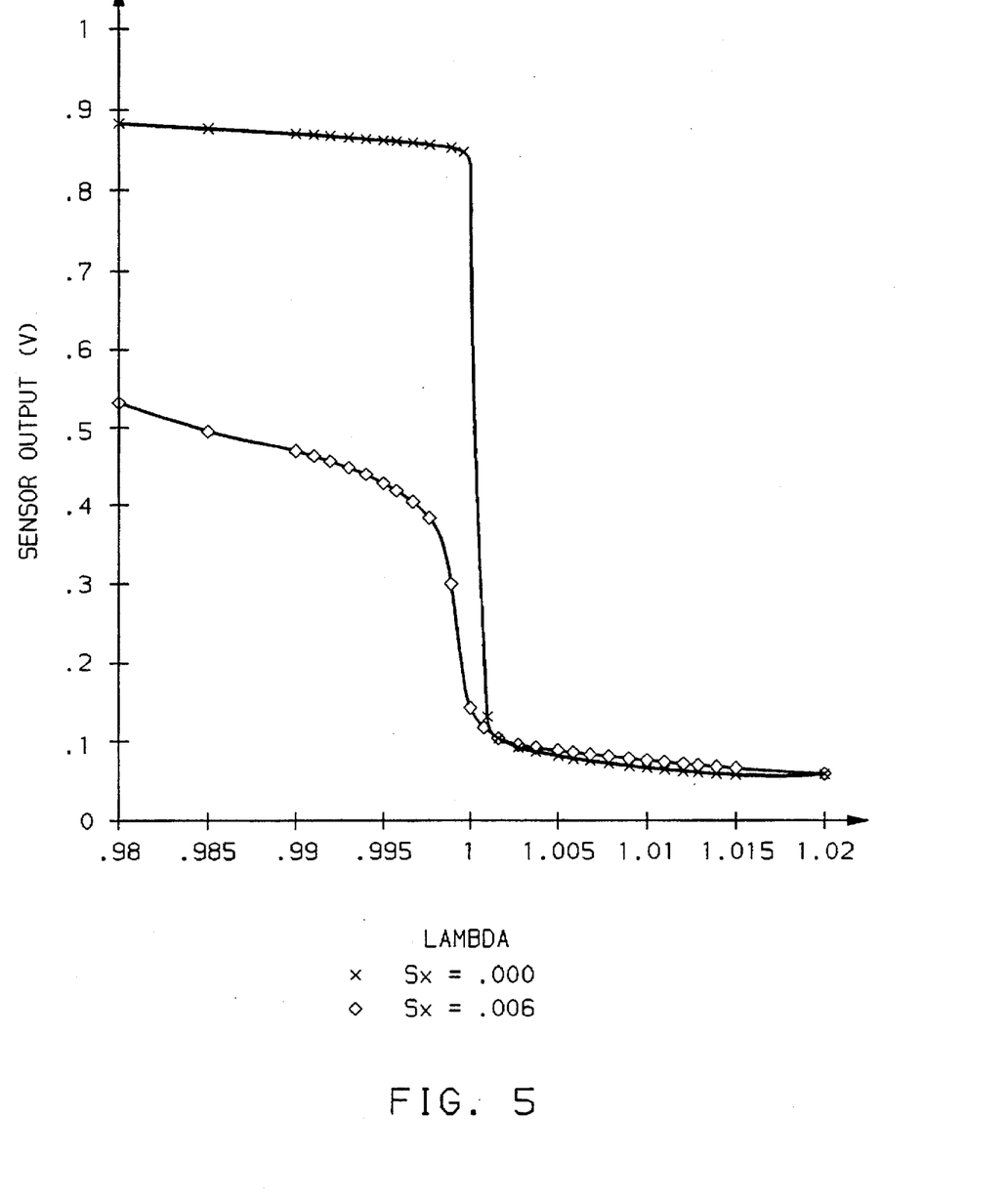
FIG. 5 is a graphic illustration of the CO sensitivity of a conical-shaped sensor without a microcomposite layer according.
Figure 7:
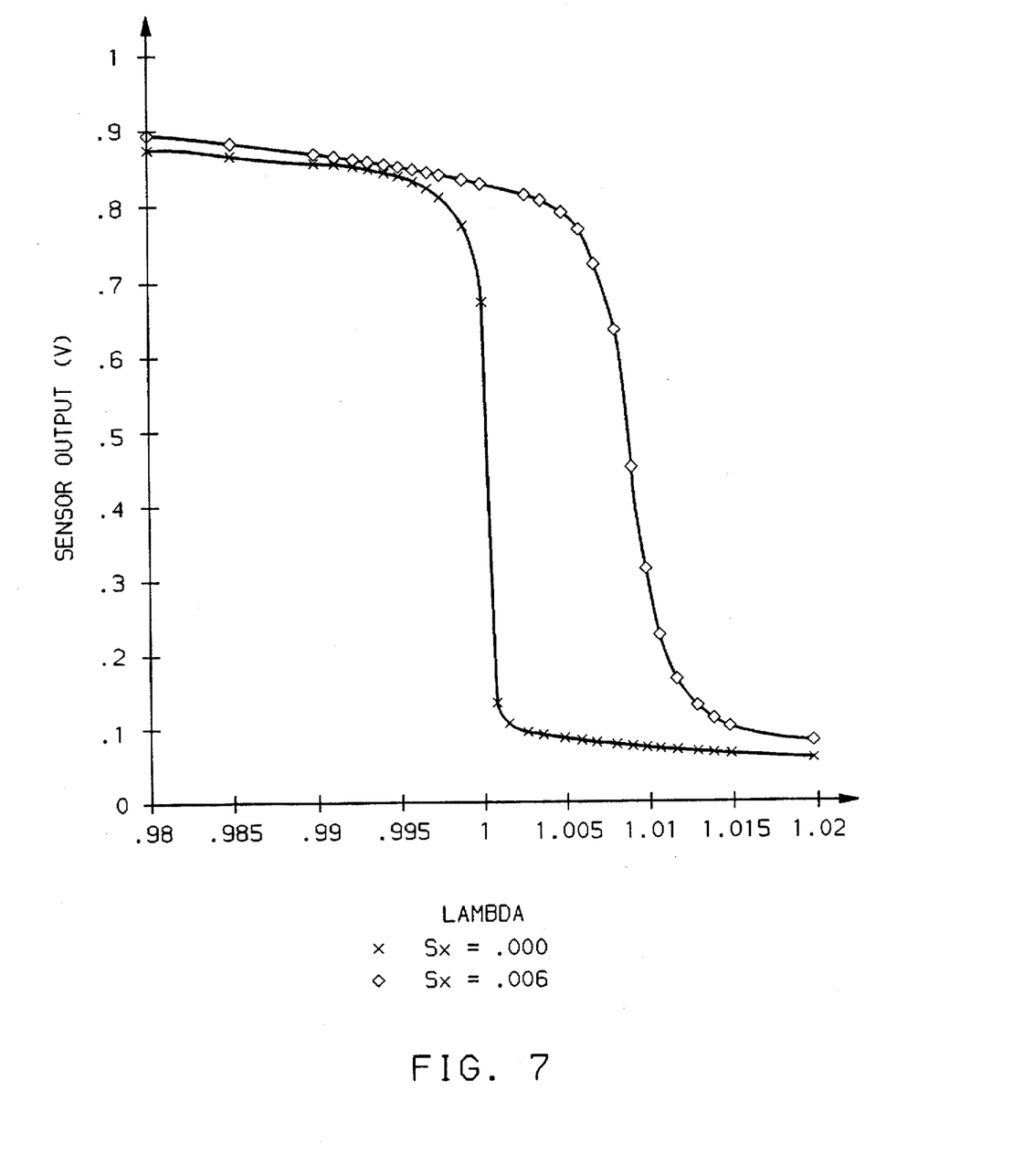
FIG. 7 is a graphic illustration of data obtained on the hydrogen sensitivity of a conical-shaped sensor without a microcomposite protective coating.

FIG. 1 illustrates an ordinary exhaust sensing device 10 including an inner platinum electrode 12, a PSZ electrolyte 14, an outer platinum electrode 16 and a porous ceramic protective coat 18. The sensor in FIG. 1 does not include a microcomposite pre-equilibration zone according to the present invention. A sensor as illustrated in FIG. 1 was used in tests run wherein the results are illustrated in FIGS. 3, 5 and 7.

Figure 2:
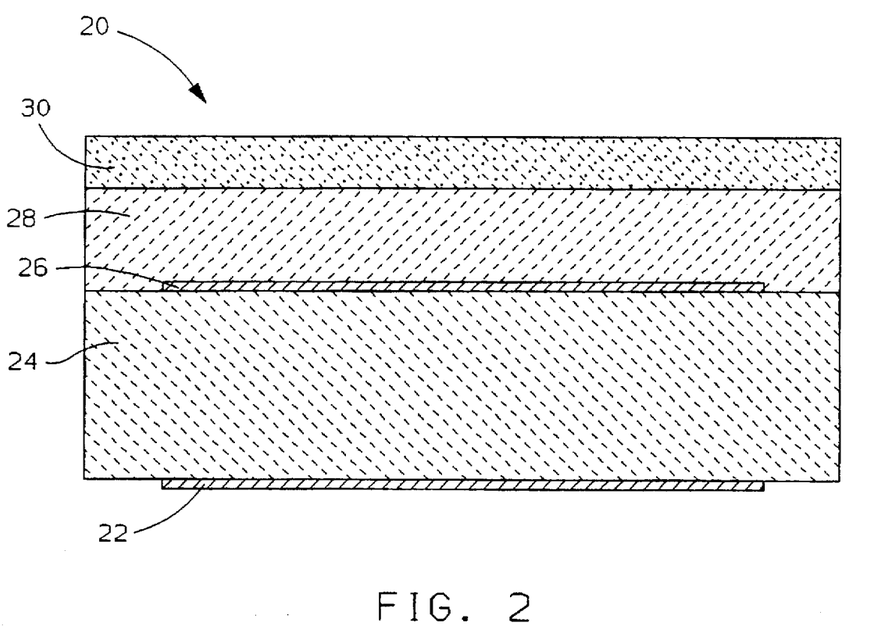
FIG. 2 is an illustration of a representative cross section of an exhaust sensor including a pre-equilibration zone according to the present invention.

FIG. 2 illustrates a sensing device 20 according to the present invention including an inner platinum electrode 22, a PS2 electrolyte 24, an outer platinum electrode 26, a porous ceramic protective coat 28 and a catalyzed microcomposite pre-equilibration zone 30. A sensor as illustrated in FIG. 2 was used in tests run wherein the results are illustrated by FIGS. 4, 6, and 8.

FIGS. 3–8 are graphical illustrations of results from gas bench testing of various sensors. Gas bench testing of sensors involves blending individual gases to form a mixture that simulates actual engine exhaust. The use of synthetic gas mixtures provides advantages over the conventional method of using actual engine exhaust for characterizing sensor performance. These advantages become more distinct when we attempt to focus in on small variations in sensor performance that are becoming more important as emission requirements and demands on control systems become tighter. Gas mixtures can be produced very precisely so that the test conditions can be very accurately controlled for highly accurate measurement of sensor performance. The test mixtures can be easily varied under controlled conditions so that the impact of these variations on sensor output can be studied. Engine exhaust, on the other hand, has an extremely variable composition that is very difficult to measure and even more difficult to control. Analysis of exhaust gas is, at best, a low resolution average of the actual composition. Because engine test conditions can not be well controlled or monitored, sensor data produced with engine exhaust does not have the resolution needed to detect these small but important performance variations.

In theory, the large voltage step produced by a stoichiometric air/fuel ratio sensor is due to the very large changes in equilibrated oxygen and combustible gas partial pressures that occur as they approach zero at the stoichiometric point. However, the combustion reactions in actual exhaust gases are not totally complete so no sharp changes in any gas concentrations are observed that correspond to the stoichiometric point. These concentrations steps are only present when the gases approach equilibrium conditions. A perfect sensor would indicate the true stoichiometric point regardless of the chemical condition of the exhaust. Actual sensors are not ideal and as a result, sensor output variations are seen when they are exposed to non-equilibrium gas mixtures. By measuring the degradation in the output of a sensor when it is exposed to known non-equilibrium mixtures, a relative rating of sensor performance can be established. This is the basic approach used in stoichiometric sensor bench testing illustrated in FIGS. 3–8.

The first step in creating a test procedure using non-equilibrium gas mixtures is to determine a method that defines the non-equilibrium conditions. It is important that the definition be complete and concise so that the test conditions can be well documented and easily communicated. It is also important to be able to easily reference and compare the test conditions to actual engine exhaust. The characteristic selected to define the gas mixtures is the Maldistribution Parameter ($S_x$). The Maldistribution Parameter is well described in Eltinge in SAE paper 680114, which is hereby incorporated by reference. All of the basic gas constituents concentrations can be completely defined at any desired air/fuel ratio by specifying the value of $S_x$, the hydrogen to carbon ratio in the original fuel, and the value of the water-gas equilibrium constant. The Maldistribution Parameter is often calculated during the emission tests so a basis for comparison to actual engine exhaust exists.

The basic gas constituents present in hydrocarbon and air combustion exhaust are: nitrogen, carbon dioxide, water, carbon monoxide, oxygen, and hydrogen. The concentrations of all six of these constituents can be defined with the parameters listed above. Unburned hydrocarbons and $NO_x$ are also present in exhaust and do have an impact on sensor performance.

The gas bench test procedure consisted of recording the sensor voltage while stepping through a series of air/fuel ratios around the stoichiometric point. The air/fuel ratios are designated by the normalized value, LAMBDA (LAMBDA is the actual Air/Fuel ratio divided by the Stoichiometric Air/Fuel ratio). Typically, the air/fuel ratio sweep is started at the fuel rich condition of 0.98 LAMBDA and is stepped in increments of 0.001 LAMBDA to the fuel lean condition of 1.02 LAMBDA. This range normally includes the sensor voltage transition but is also narrow enough to provide good resolution of the sensor's characteristics. Two simulated gasoline exhaust mixtures are often used and are designated as $S_x$=0.000 and $S_x$=0.006 (numerical values are in terms of Fuel/Air mass ratios). In both cases the hydrogen/carbon ratio of y=1.85 for standard fuel and the generally assumed standard value of K=3.5 are used in addition to the $S_x$ value to determine mixture concentrations. The $S_x$=0.000 designation defines a fully equilibrated gas mixture and the actual test gas mixture approaches this condition to within practical limits. (A true equilibrium gas mixture would have rich A/F oxygen partial pressures in the range of $10^{-20}$ atm. and lean CO and $H_2$ partial pressures in a similar range. Due to limits on gas purity, leakage, contamination, etc., these low levels can not be achieved in bulk gas mixtures.) The actual $S_x$=0.000 test gas mixture requires that some minimal level of equilibration reactions occur on the sensor surface. Experience has shown that the output curves for most "normally operating" sensors are very close to ideal when tested with the simulated $S_x$=0.000 mixtures. This test is used as an indication of the sensors "baseline" performance. The other test gas, designated $S_x$=0.006, defines a mixture that represents the highest level of non-equilibrium conditions expected to be seen in a modern engine operated near the stoichiometric point. This mixture contains significant levels of oxygen, carbon monoxide, and hydrogen simultaneously. Significant equilibration reactions must occur on the sensor surface with this test gas. An ideal sensor would produce the same output curve with both the $S_x=0.000$ and $S_x=0.006$ mixtures. The variation between the two curves provides a rating of sensor performance.

The sensor curve for the sensors are observed to shift in two areas when tested with $S_x=0.006$ gas mixtures compared to $S_x=0.000$ mixtures. As the gas composition moves further away from equilibrium, the rich voltage decreases and the sensor transition point shifts in the lean direction. These two effects appear to be caused by different phenomenon. The predominate theory is that the high diffusion rate of hydrogen relative to the diffusion rate of oxygen through the sensor's protective coating causes the lean shift. The hydrogen is oxidized on platinum surface to form water. This continuous reaction creates hydrogen and oxygen fluxes across the protective coating. The higher hydrogen diffusion rate creates an apparent rich condition at the platinum surface which shifts the transition point in the lean direction. Test data supports this theory.

The reduced rich voltages appear to be linked to the sensors ability to oxidize the excess carbon monoxide. If carbon monoxide is removed from the gas mixture, the rich voltage does not drop. Some of the excess oxygen present in rich conditions may be adsorbing on the platinum surface and not readily combining with the CO to form $CO_2$.

In each of the tests run wherein the results are illustrated in FIGS. 3–8, a porous ceramic protective coating was flame sprayed over a platinum outer electrode and zirconia electrolyte as illustrated in FIG. 1. In the examples corresponding to FIGS. 4, 6 and 8, the sensor included a post-impregnated catalyzed microcomposition produced by using a one percent by weight platinum dip as described above. In the example corresponding to FIGS. 3, 5 and 7, the sensor did not have a catalyzed microcomposite according to the present invention. Comparing FIG. 4 with FIG. 3 illustrates a dramatic reduction in lean shift which was reduced 80% by using a sensor according to the present invention. In the examples corresponding to FIGS. 5 and 6, the effect of maldistribution in the form of CO only on sensor output was measured. The effect is known as "rich voltage suppression." Comparing FIG. 6 with FIG. 5 shows a 80% reduction in rich voltage suppression according to the present invention. In FIGS. 7 and 8, the effect of maldistribution in the form of $H_2$ only on sensor output was measured. The effect is known as "hydrogen induced lean shift." Comparing FIG. 8 with FIG. 7 shows a 70% reduction in hydrogen induced lean shift using a sensor according to the present invention.

The embodiments of the invention in which an exclusive property or privilege is claimed as defined as follows:

1. An exhaust sensor comprising:
   inner and outer electrodes and a solid, porous electrolyte body between the electrodes;
   a porous protective coat overlying the outer electrode and having a thickness ranging from 50 to 500 microns;
   a microcomposite layer overlying the porous protective coat, said microcomposite layer comprising 80 to 99.998 weight percent of a ceramic oxide, and at least one catalyst material selected from the group consisting of platinum, palladium, rhodium, transition metals and mixtures thereof; wherein the catalyst material is present in an amount ranging from about 0.002 to about 20 weight percent, said microcomposite layer having a thickness ranging from 10–500 microns and sufficient to reduce hydrogen induced lean shift.

2. An exhaust sensor as set forth in claim 1 wherein the catalyst material is present in an amount ranging from about 1 to about 2 weight percent.

3. An exhaust sensor as set forth in claim 1 wherein at least one catalyst is rhodium.

* * * * *